United States Patent [19]

Bowden et al.

[11] Patent Number: 5,723,649
[45] Date of Patent: Mar. 3, 1998

[54] PREPARATION OF CYCLOPROPANE ESTERS

[75] Inventors: Martin Charles Bowden, Brighouse; Stephen Martin Brown, Cumberworth, both of United Kingdom

[73] Assignee: Zeneca Limited, London, England

[21] Appl. No.: 776,549

[22] PCT Filed: Nov. 2, 1995

[86] PCT No.: PCT/GB95/02570

§ 371 Date: Jan. 31, 1997

§ 102(e) Date: Jan. 31, 1997

[87] PCT Pub. No.: WO96/16018

PCT Pub. Date: May 30, 1996

[30] Foreign Application Priority Data

Nov. 24, 1994 [GB] United Kingdom ............... 9423743

[51] Int. Cl.$^6$ ............................................. C07C 69/74
[52] U.S. Cl. ............................................. 560/124
[58] Field of Search ....................... 560/124; 562/506

[56] References Cited

U.S. PATENT DOCUMENTS 4,113,968  9/1978  Mori ............................... 560/124

FOREIGN PATENT DOCUMENTS

94/27942  12/1994  WIPO.

Primary Examiner—Michael L. Shippen
Attorney, Agent, or Firm—Joel G. Ackerman

[57] ABSTRACT

The invention provides an improved process for the preparation of a lower alkyl ester of 3-(2-chloro-3,3,3-trifluoroprop-1-en-1-yl)-2,2-dimethylcyclopropane carboxylic acid in which the corresponding lower alkyl ester of a carboxylic acid selected from 6-bromo-6-chloro-3,3-dimethyl-7,7,7-trifluorohept-2-enoic acid and 6,6-dichloro-3,3-dimethyl-7,7,7-trifluorohept-2-enoic acid is treated with an alkali metal lower alkoxylate in the presence of an aromatic hydrocarbon solvent under conditions under which the lower alcohol of the alkoxylate is removed from the reaction mixture by distillation with the aromatic solvent. The products are useful as intermediates in the manufacture of pyrethroid insecticides.

4 Claims, No Drawings

PREPARATION OF CYCLOPROPANE ESTERS

This invention relates a novel process for making certain cyclopropane esters useful in the synthesis of valuable pesticides.

Esters of 3-(2-chloro-3,3,3-trifluoroprop-1-en-1-yl)-2,2-dimethylcyclopropane carboxylic acid with for example 3-phenoxybenzyl alcohol, α-cyano-3-phenoxybenzyl alcohol and 2-methyl-3-phenylbenzyl alcohol are important insecticidal and acaricidal products, and the simple alkyl esters of this acid are important intermediates in the manufacture of such products. It is desirable to establish novel processes for the manufacture of such intermediates in order to increase the manufacturer's flexibility to respond to fluctuations in price and availability of raw materials.

In our UK patent application no.9410362.9 we disclosed a novel process which can be used in to obtain the above-mentioned acid and its esters. That process which was for preparing a lower alkyl ester of 3-(2-chloro-3,3,3-trifluoroprop-1-en-1-yl)-2,2-dimethylcyclopropane carboxylic acid, comprised the steps of (a) reacting a compound of formula (I) with a tri-lower-alkyl orthoacetate containing up to four carbon atoms in each alkyl group in the presence of at least a catalytic amount of a acid to obtain a compound of formula (III) where R is alkyl of up to four carbon atoms, and (b) treating said compound of formula (III) with at least one molar equivalent of a base to obtain a lower alkyl ester of 3-(2-chloro-3,3,3-trifluoroprop-1-en-1-yl)-2,2-dimethylcyclopropane carboxylic acid.

If desired the carboxylic acid itself may be obtained by the further step of subjecting said lower alkyl ester to hydrolysis.

In that process the tri-lower-alkyl orthoacetate is preferably selected from trimethyl orthoacetate and triethyl orthoacetate, and the acid used in step (a) is preferably a simple carboxylic acid such as a propionic acid or butyric acid, e.g. isobutyric acid or an alkane or arene sulphonic acid e.g. p-toluene sulphonic acid. Alternatively the reaction can be conducted in the presence of an active clay, such as a montmorillonite. Montmorillonite KSF is a particularly suitable catalyst for this process. The process is carried out at an elevated temperature preferably the reflux temperature, under conditions where alcohol generated by the process can be removed from the reaction zone. The reactants are heated for a sufficient period to obtain the desired product of formula (III).

In that process the base used in step (b) is preferably a alkali metal alkoxide, and the process may be carried out in a suitable solvent or diluent such as for example a polar aprotic solvent such as dimethylformamide or an excess of the alcohol corresponding to the alkali metal alkoxide. Sodium or potassium t-butoxide are preferred bases and the reaction is preferably carried out in dimethylformamide. Other bases such as alkali metal amides, eg sodamide, or alkali metal disilylazides, eg sodium disilylazide, nay also be used, preferably in the presence of a catalytic quantity of an alkanol such as t-butanol.

In step (a) of that process the reaction of the compound of formula (I) with the trialkyl orthoacetate is believed to lead initially to a compound of formula (IV) where X is chloro or bromo and R is alkyl of up to four carbon atoms. It is possible to isolate the compounds of formula (IV) by heating the reactants for a sufficient time to obtain the compounds of formula (IV) but for less than a sufficient time to obtain the compounds of formula (III). The compounds of formula (IV) are believed not to have been previously described and in particular the following specific compounds are believed to be novel:

5-bromo-5-chloro-4-(1,1-diethoxyethoxy)-2-methyl-6,6,6-trifluorohex-2-ene, 5,5-dichloro-4-(1,1-diethoxyethoxy)-2-methyl-6,6,6-trifluorohex-2-ene, 5-bromo-5-chloro-4(1,1-dimethoxyethoxy)-2-methyl-6,6,6-trifluorohex-2-ene, and 5,5-dichloro-4-(1,1-dimethoxyethoxy)-2-methyl-6,6,6-trifluorohex-2-ene.

Under the process conditions the compounds of formula (IV) undergo a rearrangement leading to the compounds of formula (III). The compounds of formula (III) are also believed not to have been described previously and in particular the following specific compounds are believed to be novel:

ethyl 6-bromo-6-chloro-3,3-dimethyl-7,7,7-trifluorohept-4-enoate, methyl 6-bromo-6-chloro-3,3-dimethyl-7,7,7-trifluorohept-4-enoate, ethyl 6,6-dichloro-3,3-dimethyl-7,7,7-trifluorohept-4-enoate, and methyl 6,6-dichloro-3,3-dimethyl-7,7,7-trifluorohept-4-enoate.

In a further aspect of the invention disclosed in our UK Patent application no 9410362.9 there was provided a process as defined above wherein the compound of formula (I), wherein X is chloro or bromo, is obtained by a process which comprises reacting a compound of formula (II) with 3-methylbut-2-en-1-al in the presence of a strong base and an inert solvent.

Where the compound of formula (I) is 5,5-dichloro-4-hydroxy-2-methyl-6,6,6-trifluorohex-2-ene the compound of formula (II) is 1,1-dichloro-2,2,2-trifluoroethane.

Where the compound of formula (I) is 5-bromo-5-chloro-4-hydroxy-2-methyl-6,6,6-trifluorohex-2-ene the compound of formula (II) is 1-bromo-1-chloro-2,2,2-trifluoroethane. 5-Bromo-5-chloro-4-hydroxy-2-methyl-6,6,6-trifluorohex-2-ene appears not to have been previously described.

This preliminary step of that process is conducted in the presence of a strong base, which is believed to act by generating a perhaloalkyl ion which then reacts with the aldehyde. Suitable strong bases include alkali metal lower alkoxides, such as sodium or potassium isopropoxides or t-butoxides, but other bases such as alkali metal hydrides and amides may also be used, and the process is preferably conducted at lower temperatures to avoid the production of unwanted by-products. A preferred temperature is within the range −80° C. to 0° C., especially where a polar aprotic solvent is used. Particular examples of polar aprotic solvents which may be useful in the process include amides such as dimethylformamide, dimethylacetamide and di-n-butylacetamide, cyclic ethers such as tetrahydrofuran, tetrahydropyran and dioxan, glycol ethers such as ethylene glycol dimethyl ether, and ethylene glycol diethyl ether, and sulphoxides such as dimethyl sulphoxide. However other inert solvents such as aromatic hydrocarbons e.g. toluene may also be used.

The process is useful to produce the compounds of formula (I) in good yield and purity and allows for easy isolation of the desired product. Any unreacted or excess compound of formula (II) can be readily recovered and recycled.

Further particulars concerning the process disclosed in our earlier UK patent application no.9410362.9 by which the compounds of formula (I) can be made and used in the synthesis of esters of 3-(2-chloro-3,3,3-trifluoroprop-1-en-1-yl)-2,2-dimethylcyclopropane carboxylic acid are set out in the Examples A to I below.

Although the above process as described in our UK Patent Application no. 9410362.9 represents a significant improvement over the prior art processes, we have now found that by changing the conditions of step (b) even more improved yields with respect to the desired cis-Z isomers can be obtained, and at the same time the step can be conducted in a more ecommomically effective manner. In particular we have found that this can be achieved by choosing solvents which will facilitate the removal of the alcohol corresponding to the alkoxide base during step (b). This avoids using a polar aprotic base such as dimethylformamide (as described in our earlier application) which has disadvantages because the work-up procedure leads to difficulties in recovering the solvent in a reusable form.

Accordingly the present invention provides a process for the preparation of a lower alkyl ester of 3-(2-chloro-3,3,3-trifluoroprop-1-en-1-yl)-2,2-dimethylcyclopropane carboxylic acid in which the corresponding lower alkyl ester of a carboxylic acid selected from 6-bromo-6-chloro-3,3-dimethyl-7,7,7-trifluorohept-2-enoic acid and 6,6-dichloro-3,3-dimethyl-7,7,7-trifluorohept-2-enoic acid is treated with an alkali metal lower alkoxylate in the presence of an aromatic hydrocarbon solvent under conditions under which the lower alcohol of the alkoxylate is removed from the reaction mixture by distillation with the aromatic solvent.

Suitable aromatic solvents include toluene and xylene. The process is preferably conducted using sodium or potassium t-butoxide. The distillation is carried out at a pressure below atmospheric pressure.

The improved process of the invention is exemplified in Examples 1 and 2 below. Example 3 illustrates the lower yield obtained when the alcohol is not removed during the reaction is not part of the present invention and is included for comparative purposes only.

EXAMPLE A

This Example illustrates the preparation of 5,5-dichloro-4-hydroxy-2-methyl-6,6,6-trifluoro hex-2-ene.

Sodium t-butoxide (2.4 ml of a 42% solution in dry dimethylformamide) was added dropwise over a period of 20 minutes to a stirred mixture of 1,1-dichloro-2,2,2-trifluoroethane (1.38 g), 3-methylbut-2-ene-1-al (0.636 g) and dry tetrahydrofuran (30 ml) maintained at a temperature of −65° C. by external cooling under a nitrogen atmosphere, and the stirred mixture maintained at that temperature for a further 30 minutes after completion of the addition. The external cooling was removed and the reaction quenched by dropwise addition of a saturated aqueous ammonium chloride solution until the temperature had risen to −20° C. The mixture was thereafter stirred until the temperature had risen to ambient (ca.20° C.).

The aqueous and organic phases were separated and the aqueous phase extracted with dichloromethane (2×20 ml) and the extracts combined with the organic phase and dried over anhydrous sodium sulphate. After removal of the solvents by evaporation under reduced pressure the residue was dissolved in hexane (20 ml) and the solution washed with brine (3×5 ml) and dried over anhydrous sodium sulphate, and concentrated by removal of the solvent under reduced pressure. The residue was dissolved in a mixture of ethyl acetate and petroleum ether (boiling range 40°–60° C.) (1:6 parts by volume, 20 ml) and purified by loading onto a short silica column (3.75 cm) and eluting with the same mixture (400 ml). Successive fractions (3) were examined by chromatography to establish that the desired product was present in the first two fractions. The eluate was concentrated by evaporation of the solvents under reduced pressure and the residue (1.33 g) identified by nuclear magnetic resovance spectroscopy and gas chromatographic-mass spectral analysis as 5,5-dichloro-4-hydroxy-2-methyl-6,6,6-trifluorohex-2-ene.

EXAMPLE B

This Example illustrates the preparation of 5-bromo-5-chloro-4-hydroxy-2-methyl-6,6,6-trifluorohex-2-ene.

Sodium t-butoxide (1.39 g of a 42% solution in dry dimethyl formamide was added dropwise over a period of 5 minutes to a stirred mixture of 1-bromo-1-chloro-2,2,2-trifluoroethane (0.535 ml), 3-methylbut-1-en-1-al (0.538 ml) and dry tetrahydrofuran (10 ml) maintained at a temperature of −78° C. by external cooling under a nitrogen atmosphere. The mixture was then stirred for a further 40 minutes at the temperature after which the external cooling was removed and the reaction quenched by the dropwise addition of saturated aqueous ammonium chloride solution. The mixture was then partitioned between water and diisopropyl ether and the aqueous phase separated, washed with diisopropyl ether (3×25 ml), and the washings combined with the organic phase. The organic phase was washed with brine and dried over anhydrous sodium sulphate and concentrated by evaporation under reduced pressure. After purification by a procedure similar to that set out in the previous Example there was obtained 5-bromo-5-chloro-4-hydroxy-2-methyl-6,6,6-trifluorohex-2-ene (1.39 g), identified by nuclear magnetic resonance and infra-red spectroscopy.

EXAMPLE C

This Example illustrates the preparation of 5-bromo-5-chloro-4-hydroxy-2-methyl-6,6,6-trifluorohex-2-ene.

Tetrahydrofuran (230 ml) and sodium t-butoxide (57.6 g; 40% w/v solution in dimethylformamide) was charged to a split-neck reaction flask, and cooled to −60° C. with stirring. 1-Bromo-1-chloro-2,2,2-trifluorethane (47.6 g) and senecialdehyde (20.9 g) were charged simultaneously over 25 minutes, then the mixture was stirred at −60° C. for a further 30 minutes. On completion of reaction, the mass was quenched by controlled addition of saturated ammonium chloride solution (120 ml). Hexane (500 ml) was added to the mixture, then the aqueous phase was separated and extracted with further hexane (2×500 ml). The combined organics were washed with brine (2×100 ml) and then water (3×20 ml). Drying (sodium sulphate) and concentration in vacuo then gave the product 5-bromo-5-chloro-4-hydroxy-2-methyl-6,6,6-trifluorohex-2-ene as a mobile yellow oil (50.1 g, 70% yield).

$^1$H NMR: 1.30(3H,s.:CMe$_2$); 1.35(3H,s.:CMe); 1.85(1H, br.OH); 4.20 and 4.30(1H,d,CHOH diastereomers): 4.90 (1H,d.:CH). MS: 195 (CF$_3$CClBr+), 85 (M+—CF$_3$CClBr). IR: 3400 cm$^{-1}$.

EXAMPLE D

This Example illustrates the preparation of 5-bromo-5-chloro-4-(1,1-dimethoxyethoxy)-2-methyl-6,6,6-trifluorohex-2-ene 5-Bromo-5-chloro-4-hydroxy-2-methyl-6,6,6-trifluorohex-2-ene (10.0 g), trimethyl orthoacetate (48.0 g) and isobutyric acid (0.29 g) were charged to a round-bottomed flask fitted with: nitrogen inlet/bubbler, thermometer and Dean and Stark received packed with 5A molecular seives. The mixture was heated with agitation to reflux and distillates collected until reaction mass temperature increased to 111° C. (ca. 1 hr). Once the reaction was complete, the residual trimethyl orthoacetate was removed by distillation under vacuum (ca. 50° C. @ 50 mmHg) to give the product, 5-bromo-5-chloro-4-(1,1-dimethoxyethoxy)-2-methyl-6,6,6-trifluorohex-2-ene, as an orange oil (10.9 g, 85% yield).

$^1$H NMR 1.45(3H,s:MeCOMe); 1.75(3H,s:CMe$_2$); 1.85 (3H,s:CMe$_2$); 3.28(3H,s,OMe); 3.30(3H,s,OMe); 4.98 and 5.02(1H,d, CHOR—diastereomers); 5.35(1H,d,:CH). MS: 89 (MeC(COMe)$_2$+).

EXAMPLE E

This Example illustrates the preparation of methyl 6-bromo-6-chloro-3,3-dimethyl-7,7,7-trifluorohept-4-enoate.

5-Bromo-5-chloro-4-hydroxy-2-methyl-6,6,6-trifluorohex-2-ene (10.0 g), trimethyl orthoacetate (16.0 g) and Montmorillonite KSF (0.5 g) were charged to a round-bottomed flask fitted with: nitrogen inlet/bubbler, thermometer and still-head. The mixture was heated with agitation, and the methanol-trimethyl orthoacetate distillates were collected until the reactor temperature increased to 111° C. (ca. 1 hr). The reaction was then heated to 135° C. and held for a further 1 hour. The methanol/trimethyl orthoacetate distillates were recharged and the distillation procedure repeated twice. Once the reaction was complete, the Montmorillonite was removed by filtration. The residual trimethyl orthoacetate was then removed by distillation under vacuum (ca. 50° C. @ 100 mmHg) to give the product, methyl 6-bromo-6-chloro-3,3-dimethyl-7,7,7-trifluorohept-4-enoate as a brown oil (7.8 g, 59% yield).

$^1$H NMR: 1.20(6H,s;CMe$_2$); 2.40(2H,s,CH$_2$CO$_2$Me); 3.65(3H,s,OMe); 5.75(1H,d,CH); 6.45(1H,d,CH). MS: 305 (M$^+$—OMe); 257 (M+—Br). IR: 1750 cm$^{-1}$.

EXAMPLE F

This Example illustrates the preparation of ethyl 6,6-dichloro-3,3-dimethyl-7,7,7-trifluorohept-4-enoate.

A mixture of triethyl orthoacetate (25 ml), 5,5-dichloro-4-hydroxy-2-methyl-6,6,6-trifluorohex-2-ene (3.5 g), and isobutyric acid (0.11 g) was heated at the reflux temperature. The refluxing volatiles were condensed and collected in a Dean & Stark apparatus containing molecular sieves (4A) to collect the by-product ethanol and separate it from the orthoacetate which was returned to the mixture. After 30 minutes the more volatile components were removed by evaporation under reduced pressure and the residual oil (consisting principally of 5,5-dichloro-4-(1,1-diethoxyethoxy)-2-methyl-6,6,6-trifluorohex-2-ene, 3.8 g) collected. This was then heated with isobutyric acid (10 μl) at the reflux temperature for 16 hours under a condenser containing molecular sieves (4A) to remove ethanol from the condensate. The residual oil was subjected to purification by column chromatography using a 15:1 (by volume) mixture of hexane:ethyl acetate as eluant and a silica gel column (230–400 mesh, 60 Å) to obtain ethyl 6,6-dichloro-3,3-dimethyl-7,7,7-trifluorohept-4-enoate, identified by nuclear magnetic resonance, and gas chromatographic mass-spectroscopy.

EXAMPLE G

This Example illustrates the preparation of methyl 6,6-dichloro-3,3-dimethyl-7,7,7-trifluorohept-4-enoate.

A procedure similar to that described in Example 6 was used to obtain the product from a mixture of trimethyl orthoacetate (70 ml), 5,5-dichloro-4-hydroxy-2-methyl-6,6,6-trifluorohex-2-ene (10 g) and isobutyric acid (0.37 g).

EXAMPLE H

This Example illustrates the preparation of ethyl 3-(2-chloro-3,3,3-trifluoroprop-1-en-1-yl)-2,2-dimethylcyclopropane carboxylate.

A stirred solution of ethyl 6,6-dichloro-3,3-dimethyl-7,7,7-trichlorohept-4-enoate (0.1 g) in dimethylformamide (10 ml) was cooled to −25° C. under a nitrogen atmosphere and sodium t-butoxide (0.1 ml of a 42% solution in dimethylformamide) added dropwise. After 30 minutes five further drops of the sodium t-butoxide solution was added and the mixture stirred for a further 15 minutes, before the reaction was quenched with saturated ammonium chloride solution (2 ml) over a 10 minutes period. Water (40 ml) was added and the mixture extracted with hexane (3×40 ml) the combined extracts washed with brine (20 ml) and dried over anhydrous sodium sulphate. The dried solution was filtered and concentrated by evaporation under reduced pressure to give ethyl 3-(2-chloro-3,3,3-trifluoroprop-1-en -1-yl)-2,2-dimethylcyclopropane carboxylate as a mixture of isomers.

EXAMPLE I

This Example illustrates the preparation of methyl 3-(2-chloro-3,3,3-trifluoroprop-1-en-1-yl)-2,2-dimethylcyclopropane carboxylate.

By the use of a procedure similar to that described in the previous example the desired product was obtained by treating a solution of methyl 6,6-dichloro-3,3-dimethyl-7,7,7-trifluorohept-4-enoate (0.217 g) in dry dimethylformamide (10 ml) at 0° C. under a nitrogen atmosphere with sodium t-butoxide (0.2 ml of a 42% solution in dimethylformamide). The identity of the product was confirmed by gas chromatographic mass spectroscopy as consisting principally of methyl cis-3-(Z-2-chloro-3,3,3-trifluoroprop-1-en-1-yl)-2,2-dimethyl cyclopropane carboxylate.

EXAMPLE 1

This Example illustrates the preparation of methyl 3-(2-chloro-3,3,3-trifluoroprop-1-en-2-yl)-2,2-dimethylcyclopropane carboxylate under conditions where the t-butanol is removed by azeotropic distillation with toluene.

Sodium t-butoxide (2.5 g) was added quickly to a mixture of methyl 6,6-dichloro-3,3-dimethyl-7,7,7-trifluorohept-4-enoate (5.55 g, strength 91%) and toluene (50 cm$^3$) maintained under atmospheric pressure at 40° C. The resultant mixture was agitated as the pressure was reduced to 40 mm Hg and maintained at that value for 2 hours, after which the pressure was restored to atmospheric and the mixture quenched with acetic acid (4.0 cm$^3$). Sampling of the mixture by quantitative gas chromatographic analysis demonstrated that the desired product (as cis-Z isomers) was present in a yield of 75%.

EXAMPLE 2

This Example illustrates the preparation of methyl 3-(2-chloro-3,3,3-trifluoroprop-1-en-2-yl)-2,2-dimethylcyclopropane carboxylate under conditions where the t-butanol is removed by azeotropic distillation with xylene.

The procedure of the previous Example was used except that xylene (50 cm$^3$) was employed in place of toluene and the reduced pressure was 20 mm Hg, and was maintained for 2.5 hours. During this period additional xylene was added to maintain a constant volume. Sampling of the reaction mixture demonstrated the desired product (as cis-Z isomers) was obtained in a yield of 75%.

EXAMPLE 3

This Example illustrates the preparation of methyl 3-(2-chloro-3,3,3-trifluoroprop-1-en-2-yl)-2,2-dimethylcyclopropane carboxylate under conditions where the t-butanol is not removed.

The procedure of the previous Example was used except that the mixture was maintained at atmospheric pressure for the whole period of 2.5 hours. Under these conditions the yield of the desired product (as cis-Z isomers ) was only 51%.

CHEMICAL STRUCTURES
(in description)

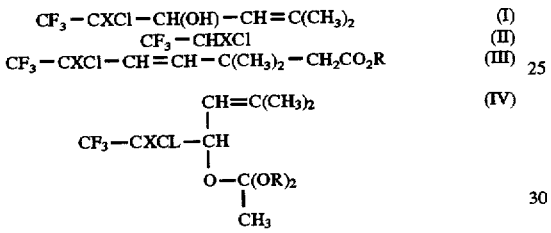

We claim:

1. A process for the preparation of a lower alkyl ester of 3-(2-chloro-3,3,3-trifluoroprop-1-en-1-yl)-2,2-dimethylcyclopropane carboxylic acid in which the corresponding lower alkyl ester of a carboxylic acid selected from 6-bromo-6-chloro-3,3-dimethyl-7,7,7-trifluorohept-2-enoic acid and 6,6-dichloro-3,3-dimethyl-7,7,7-trifluorohept-2-enoic acid is treated with an alkali metal lower alkoxylate in the presence of an aromatic hydrocarbon solvent under conditions under which the lower alcohol of the alkoxylate is removed from the reaction mixture by distillation with the aromatic solvent.

2. The process of claim 1 wherein the aromatic solvent is selected from toluene and xylene.

3. The process of claim 1 wherein the alkali metal alkoxide is sodium or potassium t-butoxide.

4. The process according to claim 1 in which the distillation is carried out at a pressure below atmospheric pressure.

* * * * *